United States Patent [19]

Johnson et al.

[11] Patent Number: 4,560,509
[45] Date of Patent: Dec. 24, 1985

[54] ANTIBIOTIC A39079 FACTOR S-1

[75] Inventors: Ronald D. Johnson; Ralph E. Kastner; LaVerne D. Boeck, all of Indianapolis, Ind.

[73] Assignee: Eli Lilly and Company, Indianapolis, Ind.

[21] Appl. No.: 552,549

[22] Filed: Nov. 16, 1983

[51] Int. Cl.$^4$ .......................................... C07D 491/08
[52] U.S. Cl. .............................. 260/239.3 P; 435/119; 435/253; 426/2
[58] Field of Search .................................. 260/239.3 P

[56] References Cited

U.S. PATENT DOCUMENTS 4,447,432  5/1984  Franceschi et al. ........... 260/239.3 P Primary Examiner—Robert T. Bond
Attorney, Agent, or Firm—Nancy J. Harrison; Arthur R. Whale

[57] ABSTRACT

A new antibiotic of the rifamycin class, A39079 factor S-1, which has the structure

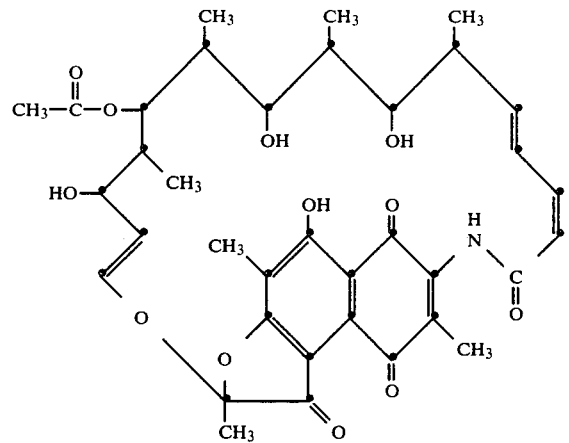

is an effective broad-spectrum antibiotic and increases feed-utilization efficiency in animals.

5 Claims, No Drawings

4,560,509

ANTIBIOTIC A39079 FACTOR S-1

SUMMARY OF THE INVENTION

This invention relates to antibiotic A39079 factor S-1, a new antibiotic of the rifamycin class which has structure 1:

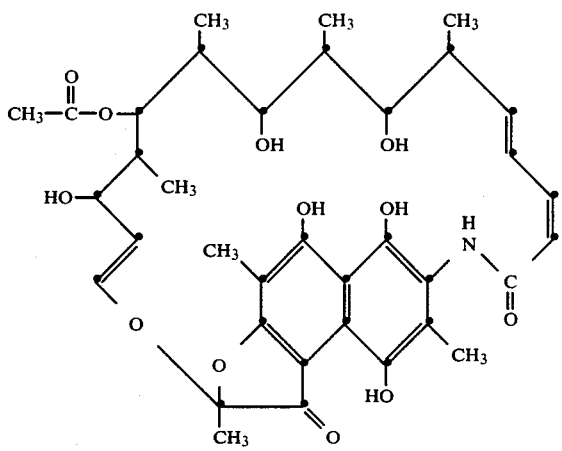

This invention further relates to a new strain of *Streptomyces spheroides* and to methods of producing A39079 factor S-1, chloramphenicol, cycloheximide (actidione), actiphenol and septacidin by culturing this new strain under submerged aerobic fermentation conditions until a substantial level of antibiotic activity is produced. Factor S-1, chloramphenicol, cycloheximide, actiphenol, or septacidin can be extracted from acidified broth filtrate with polar organic solvents, and can be further purified by extraction, chromatographic and/or crystallization techniques.

DETAILED DESCRIPTION

This invention relates to new antibiotics. In particular, this invention relates to the new rifamycin-like antibiotic A39079 factor S-1 (factor S-1) which has formula 1 and to its $C_2-C_8$-acyl ester derivatives.

Factor S-1 contains both the formula 1 compound (the reduced form) and the compound having structure 2 (the oxidized form):

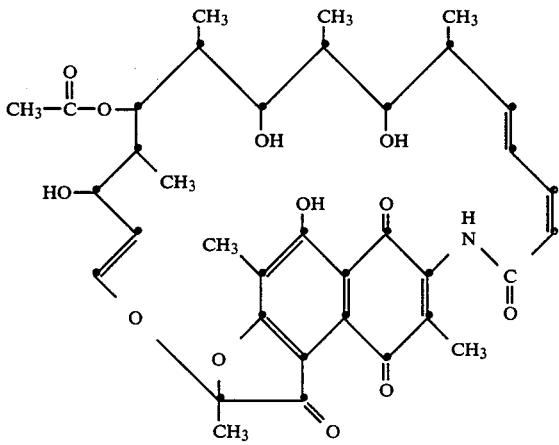

Although both compounds 1 and 2 are present in factor S-1, compound 2 (the oxidized form) is predominant in most preparations.

New, improved antibiotics are continually in demand. Better antibiotics are needed for treating human diseases, and improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

In the search for new antibiotics, structural modification of known antibiotics is attempted whenever possible. This approach is limited, howeve, to modifications which retain the desired activity. Many antibiotics, including those of the rifamycin type, have such complex structures that even small changes can be difficult to make by chemical means. The discovery of new antibiotics produced by fermentation processes continues, therefore to be of great importance even in cases where the antibiotic, once recognized, is similar to a previously known antibiotic.

Factor S-1 is a newly discovered member of the rifamycin group of antibiotics. Members of this group include rifamycin S (see, for example, U.S. Pat. No. 4,353,826).

Factor S-1 is produced by submerged aerobic fermentation of the new *Streptomyces spheroides* strain NRRL 15600, or of an S-1-producing mutant, variant or recombinant thereof. In addition to factor S-1 this culture also produces chloramphenicol, cycloheximide, actiphenol and septacidin.

A-39079 factor S-1 is a noncrystalline yellow powder which is soluble in solvents such as methanol, acetonitrile and acetone but is only slightly soluble in water. Factor S-1 in the oxidized form (2) has an empirical formula of $C_{36}H_{43}NO_{12}$ and a molecular weight of about 681. Factor S-1 has the following physical characteristics:

(1) Infrared spectroscopy: significant peaks at 3420, 3163, 1672, 1642, 1621, 1599, 1412, 1182, 1136 and 1072 $cm^{-1}$.

(2) Ultraviolet spectrophotometry: absorption maxima at 305 nm (shoulder) ($\epsilon = 16,000$), 272 nm ($\epsilon = 30,000$) and 208 nm ($\epsilon = 24,000$) in neutral and acidic methanol and at 312 nm ($\epsilon = 30,000$) and 250 nm ($\epsilon = 37,000$) in basic methanol.

(3) Titration: In 66% aqueous dimethylformamide a pKa at 8.0.

(4) Mass spectrometry: In the fast atom bombardment mode, the following results were obtained:

| M/Z | Form | | HRMS M/Z | HRMS Formula |
|---|---|---|---|---|
| 706 | $(M + Na)^+$ | reduced | 706.286 | $C_{36}H_{45}NO_{12}Na$ |
| 684 | $(M + H)^+$ | reduced | | |
| 683 | $(M)^+$ | reduced | | |
| 682 | $(M + H)^+$ | oxidized | | |
| 681 | $(M)^+$ | oxidized | | |
| 287 | indicative rifamycin chromophore fragment) | | | |

(5) Nuclear magnetic resonance spectrometry (NMR):

(a) $^{13}C$ NMR was run in deuterated chloroform, tetradeuteromethanol or hexadeuteroacetone. The resonances of protonated carbon atoms were assigned by single frequency decoupling techniques. Assignments of the other carbon atom frequencies were achieved via a fully coupled (gated) spectrum and comparison with literature values for rifamycin S. Thirty-six discrete carbon frequencies were noted which agreed with the high resolution mass spectrometric elemental analyses data. Comparison of the $^{13}C$ data for A39079 factor S-1 with that for rifamycin S indicated the three differences in substitution pattern which are shown in formulas 2 and 3.

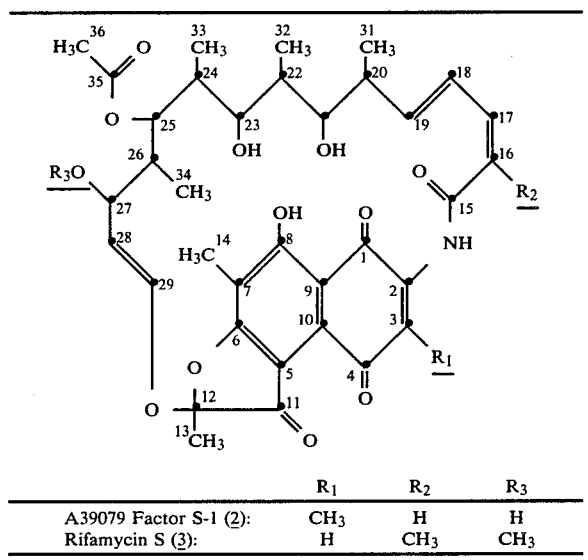

| | $R_1$ | $R_2$ | $R_3$ |
|---|---|---|---|
| A39079 Factor S-1 (2): | $CH_3$ | H | H |
| Rifamycin S (3): | H | $CH_3$ | $CH_3$ |

(b) Proton NMR was done in tetradeuteromethanol, deuterochloroform and hexadeuteroacetone. Comparison with proton NMR data for rifamycin S indicated differences in substitution at carbons 3, 16 and 27. The NMR spectrum was recorded on 360 MHz and on 270 MHz instruments and was decoupled at 360 MHz. The decoupling results indicated the presence of an ansa chain which differed from such chains in typical rifamycins at positions 16 and 27 ($R_2$ and $R_3$). The absence of a proton at position 3 on the ring ($R_1$) coupled with an aromatic methyl peak in the $^{13}C$ spectrum verified the presence of a methyl group at C-3.

(6) Elemental Analysis:

| Element | Found | Theory (for $C_{36}H_{43}NO_{12}$) |
|---|---|---|
| C | 61.05 | 63.40 |
| H | 5.66 | 6.31 |
| N | 2.31 | 2.05 |
| O | 28.23 | 28.20 |
| ash | 3.42 | 0 |

(7) Stability: Stability studies on factor S-1 in aqueous methanol solutions were run at pH levels of 2,5,7 and 9 and at temperatures of 4° C., 25° C., and 37° C. In these studies, factor S-1 was more stable in slightly acidic, neutral and basic solutions than in strongly acidic solutions (pH=2) and was most stable at 4° C., less stable at 25° C., and least stable at 37° C.

(8) Chromatography:

(a) Analytical high performance liquid chromatography (HPLC):
Column: ¼"×12.5 cm
Packing: Zorbax ODS (6μ, E. I. DuPont)
Solvent: acetonitrile:water:trifluoroacetic acid (56:43.996:0.004), pH=4.6
Flow Rate: 1 ml/min.
Detection: UV at 264 nm
Quantitation: Micromeritics 740 microprocessor with data package (Micromeritics Corp.)
Retention Time for S-1: 5.6 minutes (k'=3.74)

(b) Thin-layer Chromatography (TLC)
Adsorbent: silica gel (Whatman LKDSF plates)
Solvent: Chloroform:methanol:ammonium hydroxide (90:9.5:0.5)
Detection: UV, bioautography against *Staphylococcus aureus*
Rf Value: 0.7

As will be apparent to those skilled in the art, A39079 factor S-1 can form acyl ester derivatives. Such derivatives are useful in insolating, purifying and administering factor S-1. The pharmaceutically-acceptable acyl esters of factor S-1 are especially useful compounds of this invention. Preferred ester derivatives are those derived from a mono or di-carboxylic acid having from 2 to 18 carbon atoms, such as acetic, butyric, valeric, dodecanoic, phenylacetic, tartaric, maleic, stearic, salicylic, and sorbic acids.

The acyl ester derivatives of A39079 factor S-1 can be prepared by treating the factor with an acylating agent using conventional procedures. Suitable organic solvents for this reaction include pyridine and triethylamine. Typical acylating agents include acyl anhydrides, acyl halides (usually in combination with an acid scavenger), and active esters of organic acids. Acylation can also be achieved by using a mixture of an organic acid and a dehydrating agent such as N,N'-dicyclohexylcarbodiimide. Esterification can be monitored using standard techniques such as TLC to determine the time required for the desired reaction. Once formed, the desired ester derivatives can be separated and purified by known techniques.

This invention also relates to methods of producing factor S-1, chloramphenicol, cycloheximide, actiphenol and septacidin by culturing a new strain of *Steptomyces spheroides* under submerged aerobic fermentation conditions until a substantial level of antibiotic activity is produced. Chloramphenicol is a well known, commercially available antibacterial agent. Cycloheximide is a useful fungicidal agent (see U.S. Pat. No. 2,574,519). Septacidin is another antifungal agent. Thus, methods of making each of these compounds with the *S. spheroides* culture are additional benefits of this invention.

The *Streptomyces spheroides* culture useful for the production of antibiotic A39079 factor S-1 has been deposited and made a part of the Agricultural Research Culture Collection of the Northern Regional Research Center, U.S. Department of Agriculture, 1815 N. University St., Peoria, Ill. 61604, from which it is permanently available to the public under the accession number NRRL 15600.

THE MICROORGANISM

The new microorganism which produces factor S-1 was isolated from a soil sample collected from Vancouver, British Columbia, Canada. This organism was classified by Frederick P. Mertz of the Lilly Research Laboratories as a strain of *Streptomyces spheroides* Wallick et al. This classification was based on simultaneous laboratory comparisons, as well as a comparison with the published description of *S. spheroides* and other similar species [R. E. Buchanan and N. E. Gibbons, Eds., "Bergey's Manual of Determinative Bacteriology," 8th ed., The Williams and Wilkins Co., Baltimore, 1974; E. B. Shirling and D. Gottlieb, "Cooperative Description of Type Cultures of Streptomyces," *Int. J. Syst. Bacteriol.* 18(4):279–399 (1968)and H. Wallick, D. A. Harris, M. A. Reagan, M. Ruger, and H. B. Woodruff, "Discovery and Antimicrobial Properties of Cathomycin, A New Antibiotic Produced by *Streptomyces spheroides* N.sp., "*Antibiotics Annual* 1955-1966:909–917 (1956)].

Methods

In classifying the microorganism as a new strain of *S. spheroides*, the methods recommended by the International Streptomyces Project (ISP) for the characterization of Streptomyces species [E. B. Shirling and D. Gottlieb, "Methods of Characterization of Streptomyces species," *Int. J. Syst. Bacteriol.* 16(3), 313–340 (1966)] were followed along with certain supplementary tests.

Carbon utilization was determined with ISP No. 9 basal medium to which filter-sterilized carbon sources were added to equal a final concentration of 1.0 percent. Plates were incubated at 30° C. and read after 14 days.

Melanoid pigment production (chromogenicity) was determined with ISP No. 1 (tryptone-yeast extract broth), ISP No. 6 (peptone-yeast extract iron agar), ISP No. 7 (tyrosine agar) and modified ISP No. 7 (which has tyrosine removed).

Starch hydrolysis was determined by testing for the presence of starch with iodine on ISP No. 4 (inorganic salts-starch agar) plates (D. J. Blazevic and G. M. Ederer, "Principles of Biochemical Tests in Diagnostic Microbiology," John Wiley and Sons, Inc., New York, 1975, p. 136).

Morphology was studied using an optical light microscope. A scanning electron microscope was used to study the spore surface ornamentation.

NaCl tolerance was measured by adding NaCl to ISP No. 2 agar to equal the concentration desired.

ISCC-NBS Centroid Color Charts, standard sample No. 2106 (U.S. Department of Commerce, National Bureau of Standards, 1958) and the Color Harmony Manual (4th edition, Color Standards Department, Container Corporation of America, Illinois, 1958) were used to assign color names.

The presence of diaminopimelic acid (DAP) isomers and the presence of carbohydrates in hydrolysates of whole cells were established by the chromatographic methods of Becker et al. and Lechevalier, respectively [B. Becker, M. P. Lechevalier, R. E. Gordon and H. A. Lechevalier, "Rapid Differentiation Between Nocardia and Streptomyces by Paper Chromatography of Whole Cell Hydrolysates," *Appl. Microbiol.* 11: 421–423 (1964); and M. P. Lechevalier, "Identification of Aerobic Actinomycetes of Clinical Importance," *J. Lab. Clin. Med.* 71:934–944 (1968)].

Similarity coefficients were calculated from the equation $S = [N_s^+ + N_s^-]/[N_s^+ + N_s^- + Nd] \times 100$, where $N_s^+$ is the number of positive similarities, $N_s^-$ is the number of negative similarities, and Nd is the number of dissimilarities (differences), see W. Kurylowicz, A. Paszkiewicz, W. Woznicka, W. Kurzatkowski, "Numerical Taxonomy of Streptomycetes," Polish Medical Publishers, Warsaw, 1975.

Cultural Characteristics

The culture is characterized by an abundant aerial and vegetative growth produced on a variety of media. The spore mass is predominately in the yellow(Y) color series. The nearest matching tab is 2ba Pale Yellow [H. D. Tresner H. D. and E. J. Backus, "System of Color Wheels for Streptomycete Taxonomy," *Appl. Microbiol.* 11:335–338 (1956)]. This is best observed on glycerol-asparagine agar (ISP No. 5). This color is not constant and will vary.

The reverse side of this culture has no distinctive pigments. It is yellow-brown and is unaffected by pH. No soluble pigment is produced except that a very light brown pigment occurs when grown on ISP No. 2 and ISP No. 3 agar media.

The culture appears to be a stable homogeneous isolate. Cultural information is summarized in Table I.

TABLE I

Cultural Characteristics of NRRL 15600 and *S. spheroides*[a]

| | | NRRL 15600 | S. spheroides |
|---|---|---|---|
| ISP No. 2 | G[a]: | Abundant | Good |
| | R: | 77 m.yBr | 87.mY |
| | Am: | Abundant (Y) | Fair (W) |
| | | 1 db p.yGN. | b White |
| | Sp: | Light Brown | None |
| ISP No. 3 | G: | Fair (spotty) | Fair |
| | R: | 79.1.gy yBr | 89.p.Y |
| | Am: | Good (GN) | Good (Y) |
| | | 1½ ge | 2ba pale Y |
| | | 1.gy Olive | |
| | Sp: | Very lt Br | None |
| ISP No. 4 | G: | Abundant | Good |
| | R: | 79.1.gy.yBr | 87.m.Y |
| | Am: | Good (Y) | Good (Y) |
| | | 1½ ec p.yGN | 2ba pale Y |
| | Sp: | None | |
| | None | | |
| ISP No.5 | G: | Abundant | Abundant |
| | R: | 70.1.OY | 70.1.OY |
| | Am: | Abundant (Y) | Abundant (Y) |
| | | 2ba pale Y | 2ba pale Y |
| | Sp: | None | None |
| ISP No. 7 | G: | Abundant | Abundant |
| | R: | 76.1yBr | 70.1.OY |
| | Am: | Abundant (Y) | Abundant (Y) |
| | | 2ba Pale Y | 2ba Pale Y |
| | Sp: | None | None |
| Czapek's Sol. Agar | G: | Fair. | Good |
| | R: | 73 p.OY | 70.1.OY |
| | Am: | Poor(spotty) (Y) | Good (Y) |
| | | 2ba pale Y | 2ba pale Y |
| | Sp: | None | None |
| Emerson's | G | Abundant | Abundant |
| | R: | 55.s.Br | 71.m.OY |
| | Am: | Abundant (W) | Abundant (W) |
| | | b White | b White |
| | Sp: | None | None |
| TPO | G | None | Good |
| | R: | — | 71.m.OY |
| | Am: | — | Fair (W) |
| | | | b White |
| | Sp: | — | None |

[a] G = Growth;
R = Reverse;
Am = Aerial mycelia;
Sp = soluble pigment

Morphological Characteristics

The culture produces a well developed nonfragmenting mycelium which is monopodially branched. Sporophores are arranged in long open spirals with five or more coils. No sporangia, sclerotia, or motile spores were observed. The culture is placed in the Spirales (S) section of Pridham et al. [T. G. Pridham, C. W. Hesseltine, and R. C. Benedict, "A Guide for the Classification of Streptomycetes According to Selected Groups," *Appl. Microbiol.* 6:52–79 (1957)].

Spiral morphology is observed on all media where aerial hyphae are formed. It is especially well developed on ISP No. 5 agar medium. Mature spore chains contain 50 or more spores.

The spore shape is oblong. The spore size, as determined from scanning electron micrographs, ranges from 1.0–1.4 μM in length and 0.6–0.8 μM in width. The average size is 0.7×1.1 μM. The spore surface ornamentation is smooth.

Physiological Characteristics

Whole-cell hydrolysates contain LL-diaminopimelic acid (DAP) with neither meso nor hydroxy isomers present. Sugars present in whole-cell hydrolysates are: glucose, mannose, ribose and rhamnose. This represents a Type I cell wall and an NC or no characteristic sugar pattern (see Lechevalier, supra). This combination of major cell-wall constituents is indicative of the genus Streptomyces (see Buchanan et al. and Lechevalier, supra).

The carbon-utilization pattern for the culture is as follows: D-glucose, D-arabinose, cellobiose, D-fructose, D-galactose, maltose, D-mannitol, L-rhamnose, ribose, salicin, and D-xylose are utilized for growth; L-arabinose, i-inositol, lactose, melibiose, raffinose, and sucrose do not support growth. Table II summarizes this data.

TABLE II
Utilization of Carbon Compounds by NRRL 15600 and *S. spheroides*

| Carbon Compound | NRRL 15600 | S. spheroides |
|---|---|---|
| Control | − | − |
| D-Glucose | + | + |
| D-Arabinose | + | − |
| L-Arabinose | − | (±) |
| Cellobiose | + | + |
| Fructose | + | + |
| D-Galactose | + | + |
| i-Inositol | − | − |
| Lactose | − | − |
| Maltose | + | + |
| D-Mannitol | + | + |
| Melibiose | − | + |
| Raffinose | − | − |
| L-Rhamnose | + | + |
| Ribose | (±) | + |
| Salicin | + | + |
| Sucrose | − | + |
| D-Xylose | + | + |

−no utilization
+utilization
±doubtful utilization

The culture produces catalase, decomposes casein and esculin, liquefies gelatin, partially reduces nitrate, and hydrolyzes starch. It will tolerate the presence of up to 1 percent NaCl and will grow at temperatures from 15°–37° C.

The culture is unable to decompose hypoxanthine, tyrosine, and xanthine, does not produce melanoid pigments, and gives a variable reaction with skim milk. It is resistant to chloromycetin, lincomycin, nalidixic acid, rifampin, and sulfamethoxazoletrimethoprim, but is sensitive toward bacitracin, cephalothin, erythromycin, gentamicin, neomycin, novobiocin, penicillin G, polymyxin B, streptomycin, sulfadiazine, tetracycline, and vancomycin.

SPECIES DETERMINATION

Cultural, morphlogical, and physiological characteristics were used to select similar species from published descriptions in the literature [Buchanan et al., supra; Kurylowicz eta l., supra; Eberhard Kuster "Simple Working Key for the Classification and Identification of Named Taxa Included in the International *Streptomyces Project,*" *Int. J. Syst. Bacteriol.* 22(3):139–148 (1972); Hideo Nonomura, "Key for Classification and Identification of 458 Species of the Streptomyces Included in ISP," *J. Ferment. Technol.* 52(2):78–92 (1974); I. M. Szabo, et al., "A Diagnostic Key for the Indentification of "Species" of Streptomyces and Streptoverticillium Included in the International Streptomyces Project," *Acta Botanica Academiae Scientiarium Hungaricae* 21(3–4), 387–418 (1975); and S. A. Waksman, "The Actinomycetes Vol. II," The William and Wilkins Co., 1961, Baltimore]. The following seven Streptomyces species, closely resembled this culture and were examined with it in simultaneous laboratory comparisons:

Streptomyces almquisti[a]
Streptomyces chrestomyceticus[b]
Streptomyces longisporus flavus[c]
Streptomyces niveus[d]
Streptomyces pseudogriseolus[c]
Streptomyces rangoon[a]
Streptomyces spheroides[c]

[a]E. B. Shirling and D. Gottlieb, "Coooperative Description of Type Cultures of *Streptomyces*," *Int. J. Syst. Bacteriol.* 19(4):375–390 (1969)
[b]E. B. Shirling and D. Gottlieb, ibid 22(4): 265–394 (1972)
[c]E. B. Shirling and D. Gottlieb, ibid. 18(4): 279–399 (1968)
[d]E. B. Shirling and D. Gottlieb, ibid. 18(2): 69–189 (1968)

These cultures are reported in the literature as belonging in the yellow (Y) or white (W) color series, with spiral (S) sporophore morphology, smooth (sm) spore surface ornamentation, not producing melanoid pigments, and having a carbon-utilization pattern and cultural characteristics similar to those of the NRRL 15600 culture. The following descriptions are given to support the conclusions of this study.

1. *Streptomyces almquisti* and *S. rangoon:* In almost every comparative test run these two cultures gave identical results. The cultural characteristics are indistinguishable. The coefficient of similarity between *S. almquisti* and *S. rangoon* is 95. There remains no question that these cultures are identical strains. This conclusion is confirmed by the fact that both are listed in the ATCC Catalogue of Strains as strains of *Streptomyces albus*. It would appear, then, that *almquisti* and *rangoon* are non-valid species names and should be discontinued. The NRRL 15600 culture differs culturally, morphologically, and physiologically from these *S. albus* cultures. Culturally, the NRRL 15600 culture is more in the yellow series, while *S. albus* is in the white color series. Morphologically, the cultures are quite different, *S. albus* having tight balled coils and NRRL 15600 having long open spirals of five or more coils. The antibiotic sensitivity, carbon utilization, hypoxanthine and xanthine decomposition, NaCl tolerance, nitrate reduction, starch hydrolysis, temperature range, and skim-milk reaction of the *S. albus* strains all differ from those of NRRL 15600. There are not enough similarities to consider the NRRL 15600 culture a strain of *S. albus*.

2. *Streptomyces chrestomyceticus:* The cultural and physiological differences between this culture and the NRRL 15600 culture are sufficient to set them apart as distinct species. Large differences were noted in antibiotic sensitivity and carbon-utilization patterns. Decomposition of various substrates, NaCl tolerance, temperature range and skim-milk action also were different. The sporophores of *S. chrestomyceticus,* although spiralled, have fewer coils than those of NRRL 15600.

3. *Streptomyces longisporusflavus:* This culture is culturally distinct from NRRL 15600. The culture is very poor in formation of aerial mycelia; when formed, the mycelia differ from the mycelia of NRRL 15600. This culture produces a soluble pigment, whereas NRRL 15600 does not. The morphology of the sporophores, when present, is similar to that of the NRRL 15600 sporophores. *S. longisporusflavus* forms coremia on Czapek's solution agar. The two cultures differ significantly in physiological properties. Antibiotic sensitivity, carbon utilization, hypoxanthine and xanthine decomposition, NaCl tolerance, temperature range, and action on skim milk were among the differences observed. The similarities between *S. longisporusflavus* and the NRRL 15600 culture are insufficient to consider them the same species.

4. *Streptomyces pseudogriseolus:* This culture is significantly different from the NRRL 15600 culture under laboratory conditions. The cultures have different antibiotic sensitivity and carbon-utilization patterns. Tyrosine, hypoxanthine and xanthine are decomposed by *S. pseudogriseolus* but not by NRRL 15600. *S. pseudogriseolus* does not reduce nitrate. *S. pseudogriseolus* tolerates 9 percent NaCl and grows over a temperature range of 10°–45° C.; the NRRL 15600 culture tolerates only 1 percent NaCl and grows over a temperature range of 15°–37° C. *S. pseudogriseolus* produces an abundant aerial mycelium which is in the gray (GY) color series. The spore-surface ornamentation of *S. pseudogriseolus* is spiny. A distinctive reverse pigment is observed on several media. These cultural and physiological differences set this species apart from the NRRL 15600 culture.

5. *Streptomyces niveus* and *S. spheroides:* In almost every comparative test, these cultures give identical results. A similarity coefficient based on 117 characters is 95.7. In addition, they both produce novobiocin. There remains no question that these cultures are identical.

The NRRL 15600 culture is similar to *S. spheroides* culturally, morphologically and physiologically. Both belong in the yellow color series. This is readily observed on ISP media Nos. 5 and 7. Both exhibit white aerial color on Ermerson's agar. The reverse sides are basically yellow brown. Morphologically they are the same. Sporophores have long open spirals of five or more coils. Both have smooth oblong spores. The antibiotic sensitivity pattern, decomposition of hypoxanthine and xanthine, tolerance of NaCl, reduction of nitrate, and range of temperature do not match. The carbon-utilization pattern, although not identical, is in good agreement. Decomposition of esculine, casein, hydrolysis of starch, liquefaction of gelatin, and the inability to decompose tyrosine or produce melanoid pigments are the same in both cultures. The coefficient of similarity between NRRL 15600 and *S. spheroides* is 78. These similarities and differences are summarized in Tables III and IV.

TABLE III

Comparison of NRRL 15600 and *Streptomyces spheroides*

| Similarities | Differences |
|---|---|
| Carbon utilization | Antibiotic sensitivity |
| Catalase positive | Decomposition of hypoxanthine |
| Cultural characteristics | Decomposition of xanthine |
| Decomposition of casein | NaCl tolerance |
| Decomposition of esculin | Nitrate reduction |
| Decomposition of tyrosine | Temperature range |
| Gelatin liquefaction | |
| Melanoid pigments absent | |
| Morphology of sporophores(S) | |
| Spore chain length | |
| Spore shape | |
| Spore surface ornamentation (sm) | |
| Starch hydrolysis | |

TABLE IV

Comparison of NRRL 15600 and *S. spheroides* Characteristics

| Characteristic | NRRL 15600 | S. spheroides |
|---|---|---|
| Aerial spore mass color | (Y) | (Y) |
| Carbon utilization: | | |
| D-arabinose | + | − |
| melibiose | − | + |
| sucrose | − | + |
| Catalase production | + | + |
| Decomposition of casein | + | + |
| Decomposition of esculin | + | + |
| Decomposition of hypoxanthine | − | + |
| Decomposition of tyrosine | − | − |
| Decomposition of xanthine | − | + |
| Distinctive pigments | − | − |
| Gelatin liquefaction | + | + |
| Growth characteristics | + | + |
| Melanoid pigmentation | | |
| ISP No. 1 | ± | − |
| ISP No. 6 | − | − |
| ISP No. 7 | − | − |
| Morphology | (S) | (S) |
| NaCl tolerance (percent) | 1 | 7 |
| Nitrate reduction | ± | − |
| Reverse color | yBr | yBr |
| Skim milk | Variable | + |
| Soluble pigments | − | − |
| Spore chain length | >10 | >10 |
| Spore shape | oblong | oblong |
| Spore surface ornamentation | (Sm) | (Sm) |
| Starch hydrolysis | + | + |
| Temperature range °C. | 15–37 | 4–34 |

These comparisons indicate that NRRL 15600, although not identical, is very similar to *S. spheroides*. The differences are insufficient to distinquish NRRL 15600 as a separate species. The NRRL 15600 culture is classified, therefore, as a strain of *Streptomyces spheroides* Walleck, Harris, Reagan, Ruger and Woodruff 1956, ATCC 23965, NRRL 2449. *S. spheroides* is recognized in the Approved List of Bacterial Names [V. B. D. Skerman, et al, "Approved Lists of Bacterial Names," *Int. J. Syst. Bacteriol.* 30(1): 255–420 (1980)] and, consequently, is a validly published species.

As is the case with other organisms, the characteristics of the factor S-1-producing culture *Streptomyces spheroides* NRRL 15600 are subject to variation. For example, artificial variants and mutants of the NRRL 15600 strain may be obtained by treatment with various known mutagens such as utraviolet rays, X-rays, high-frequency waves, radioactive rays, and chemicals. All natural and artificial variants, mutants and recombinants of *Streptomyces spheroides* NRRL 15600 which retain the characteristic of factor S-1 production may be used in this invention.

Factor S-1, chloramphenicol, cycloheximide, actiphenol and septicidin are prepared by culturing *Strepto-* myces spheroides NRRL 15600, or a variant, mutant or recombinant thereof which produces these compounds, under submerged aerobic conditions in a suitable culture medium until substantial antibiotic activity is produced. The culture medium used to grow *Streptomyces spheroides* NRRL 15600 can be any one of a number of media. For economy in production, optimal yield, and ease of product isolation, however, certain culture media are preferred. Thus, for example, preferred carbon sources in large-scale fermentation include carbohydrates such as glycerol and potato dextrin. Preferred nitrogen sources include enzyme digests of casein, cottonseed meal, soybean grits, protein peptones and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M. W. about 2000) to large-scale fermentation media if foaming becomes a problem.

For production of substantial quantities of factor S-1, chloramphenicol, cycloheximide, actiphenol, and septicidin, submerged aerobic fermentation in tanks is preferred. Small quantities of these compounds may be obtained by shake-flash culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a large tank. The medium used for the vegetative inoculum can be the same as that used for larger fermentations, but other media can also be used.

*S. spheroides* NRRL 15600 can be grown at temperatures between about 15° and about 37° C. Optimum antibiotic production appears to occur at temperatures of about 30° C.

As is customary in aerobic submerged culture processes, sterile air is bubbled through the culture medium. For efficient antibiotic production in tanks the dissolved oxygen level should be maintained at about 30% of air saturation or above (at 30° C. and one atmosphere of pressure).

Antibiotic production can be followed during the fermentation by testing samples of the broth against organisms known to be sensitive to these antibiotics. One useful array organism is *Staphylococcus aureus* ATCC 9144. The bioassay is conveniently performed by an automated turbidimetric method. In addition, antibiotic production can be readily monitored by HPLC with UV detection.

Folllowing its production under submerged aerobic fermentation conditions, factor S-1 can be recovered from the fermentation medium by methods used in the art. In the recovery process the fermentation broth is usually first filtered to remove mycelia. The filtered broth can then be further purified to give the desired antibiotic. A variety of techniques may be used in this purification. A preferred technique for purification of the filtered broth involves adjusting the broth to about pH 2, adsorbing the broth on a suitable adsorbent such as a high porosity macroreticular polymer, eluting the factor from the adsorbent with a solvent such as acetonitrile, concentrating the eluate, and again extracting with a suitable solvent such as ethyl acetate. Further purification involves the use of extraction, chromatographic and/or precipitation techniques.

Alternatively, the culture solids, including medium constituents and mycelium can be used without extraction or separation, but preferably after removal of water, as a source of factor S-1. For example, after production of factor S-1 antibiotic activity, the whole fermentation broth or the broth filtrate can be dried by lyophilization, by drum-drying, or by azeotropic distillation and drying. The dried whole broth or dried broth filtrate can then be mixed directly into feed premix.

A39079 factor S-1 inhibits the growth of a broad spectrum of pathogenic bacteria, especially gram-positive bacteria. Table V summarizes the minimal inhibitory concentrations (MIC) at which factor S-1 inhibits certain organisms as determined by standard agar-dilution assays. In Table V, the activity of factor S-1 is compared with that of rifampin.

TABLE V

| In Vitro Activity of Factor S-1 | | |
|---|---|---|
| | MIC ($\mu$g/ml) | |
| Organism | Rifampin | Factor S-1 |
| *Staphylococcus aureus* NRRL B313 | 0.03 | 0.015 |
| *Staphylococcus aureus* V41 | 0.015 | 0.015 |
| *Staphylococcus aureus* X400 | 0.06 | 0.06 |
| *Staphylococcus aureus* S13E | 0.03 | 0.015 |
| *Staphylococcus epidermidis* EPI1 | 0.06 | <0.008 |
| *Staphylococcus epidermidis* 222 | 0.06 | <0.008 |
| *Streptococcus pyogenes* C203 | 0.25 | —[a] |
| *Streptococcus pneumoniae* Park 1 | 0.125 | <0.008 |
| *Streptococcus faecium* ATCC 9790 | 2 | 1 |
| *Streptococcus* sp. group D 9960 | 2 | 1 |
| *Haemophilus influenzae* C.L. | — | 0.25 |
| *Haemophilus influenzae* 76 | — | 0.125 |
| *Escherichia coli* N10 | 16 | 8 |
| *Escherichia coli* EC14 | 16 | 16 |
| *Escherichia coli* TEM | 128 | >128 |
| *Klebsiella pneumoniae* X26 | 16 | 32 |
| *Klebsiella pneumoniae* KAE | 32 | 16 |
| *Klebsiella pneumoniae* X68 | 16 | 16 |
| *Enterobacter aerogenes* C32 | 32 | 16 |
| *Enterobacter aerogenes* EB17 | 32 | 32 |
| *Enterobacter cloacae* EB5 | 32 | 32 |
| *Enterobacter cloacae* 265A | 32 | 32 |
| *Salmonella typhi* X514 | 16 | 32 |
| *Salmonella typhi* 1335 | 16 | 32 |
| *Pseudomonas aeruginosa* X528 | 16 | 16 |
| *Pseudomonas aeruginosa* X239 | 16 | 16 |
| *Pseudomonas aeruginosa* Ps18 | >128 | >128 |
| *Pseudomonas aeruginosa* Ps72 | — | 16 |
| *Serratia marcescens* X99 | 32 | 32 |
| *Serratia marcescens* SE3 | 64 | 16 |
| *Shigella sonnei* N9 | 16 | 8 |
| *Proteus morganii* PR15 | 32 | 8 |
| *Proteus inconstans* PR33 | 16 | 8 |
| *Proteus rettgeri* C24 | 8 | 2 |
| *Citrobacter freundii* CF17 | 16 | 16 |
| *Acinetobacter calcoaceticus* AC12 | — | 2 |

[a]Not tested

Another important property of factor S-1 is its ability to improve feed-utilization efficiency in ruminants. Animals having a developed rumen function utilize feed by first degrading the carbohydrate (the main nutritive portion) to pyruvate. The pyruvate is further metabolized to volatile fatty acid (VFA) derivatives, which include acetate, propionate and butyrate. It is known that the efficiency of carbohydrate utilization in ruminants is increased by treatments which stimulate the animals' rumen flora to produce propionate compounds rather than acetate or butyrate compounds. Feed-utilization efficiency can also be improved by inhibiting methane production. When methane gas is produced in the rumen, it is generally lost through eructation. This energy loss can be minimized by inhibiting methane formation.

The efficiency of feed use can be monitored by observing the production and concentration of propionate compounds in the rumen using methods described by Beck et al. in U.S. Pat. No. 4,333,923 (see especially columns 6–7). Table VI shows the ratio of volatile-fatty-acid (VFA) concentrations in factor S-1-treated flasks to concentrations in control flasks in this test.

TABLE VI

Ruminant Feed-Utilization
Activity of Factor S-1
Ratio of Treated to Control

| Dose (ppm) | mMoles/Day | | | | |
| --- | --- | --- | --- | --- | --- |
| | acetic | propionic | butyric | Total VFA | methane |
| 0.5 | 1.22 | 1.52 | 0.67 | 1.18 | 1.03 |
| 1 | 1.27 | 1.75 | 0.59 | 1.22 | 0.98 |
| 2 | 1.15 | 1.63 | 0.46 | 1.06 | 1.09 |
| 5 | 1.16 | 1.39 | 0.66 | 1.07 | 0.50 |

| Dose (ppm) | Molar Percent | | |
| --- | --- | --- | --- |
| | acetic | propionic | butyric |
| 0.5 | 1.04 | 1.29 | 0.57 |
| 1 | 1.05 | 1.49 | 0.48 |
| 2 | 1.08 | 1.55 | 0.43 |
| 5 | 1.07 | 1.30 | 0.62 |

Thus, one method of this invention comprises orally administering to ruminant animals which have a developed rumen function a propionate-increasing or methane-inhibiting amount of a formula 1 compound. Increase in propionate production and inhibition of methane production may be, and usually are, attained by the same administration.

The amount of compound to be administered for this method is usually in the range of from about 0.10 mg of compound per kg of body weight per day, to about 4.0 mg/kg/day. A preferred range is from about 0.25 mg/kg/day to about 2.75 mg/kg/day.

Yet another important property of factor S-1 is its ability to improve feed-utilization efficiency in monogastric animals. Commercially important monograstric animals include chickens and pigs. In addition, young ruminants, especially those still unweaned, function as monogastric animals. In the monogastric animal, bacteria and the host compete for nutrients in the digestive process. Agents which cause the bacteria to use less efficient substrates, leaving more efficient substrates such as glucose for the host animal, increase the feed-utilization efficiency of the host animal. Factor S-1 has such an effect, i.e., it prevents the consumption of glucose by bacteria normally present in the monogastric digestive system.

Thus, another method of this invention comprises orally administering to monogastric animals a glucose-sparing amount of a formula 1 compound. The amount of compound to be administered for this method is usually in the range of from about 0.1 mg of compound per kg of body weight per day to about 15.0 mg/kg/day. A preferred range is from about 0.6 mg/kg/day to about 6.0 mg/kg/day.

Those skilled in the animal husbandry art will understand that optimum administration rates for these methods vary, depending on the condition of the animals, their age, the food they are eating, and the purpose for which the animals are maintained.

In ruminants the formula 1 compound must be administered so that it will be present in the rumen. One way to accomplish this, especially in animals which are on pasture, is to administer the compound in the form of a sustained-release bolus. Such boluses can be made as tablets, ideally with a means to delay the dissolution of the compound over a prolonged period of time. Boluses may be made to release the compound steadily over long periods of time, even 100 days or more. A number of polymeric substances have been used to prepare such boluses; particularly effective polymers are the copolymers of polylactic and polyglycolic acids. It is necessary to retain the bolus in the rumen so that it is not carried out of the digestive tract. This can be accomplished by making the bolus of a high-density substance, such as by mixing metal particles into the composition, or by providing wings which open in the rumen and make the bolus too large to get through the opening into the animal's omasum. Such boluses should release from about 0.1 mg of compound per kg of body weight per day to about 4 mg/kg/day, preferably from about 0.25 to about 2.75 mg/kg/day.

Mineral blocks are another advantageous form in which to administer the compounds, particularly to animals on pasture or range. The usual blocks are highly compressed forms of physiologically-desirable salts and nutritive substances, which generally include phosphates, carbonates, halides, calcium salts, trace elements such as zinc, cobalt, manganese and the like, vitamins, steroids, and lubricants and binders to assist in compression. Although mineral blocks are old in the animal husbandry art, the addition of a compound of this invention provides novel blocks which are important embodiments of this invention. The compound should be added to the block in concentrations from about 200 mg/kg (0.02%) to about 500 mg/kg (0.05%), preferably from about 400 mg/kg (0.04%) to about 1500 mg/kg (0.15%).

The compounds may also be mixed into protein blocks for administration to animals. Such blocks are known, and consist of a mixture of molasses and urea, with other protein sources optionally added as well, and are supplied to animals such as, for example, ruminants to be eaten at will. Protein blocks containing a compound of this invention should contain from about 200 mg/kg (0.02%) to about 7,000 mg/kg (0.7%), preferably from about 400 mg/kg (0.04%) to about 3000 mg/kg (0.3%).

The compounds of this invention may also be orally administered in pharmaceutical dosage forms, such as tablets, capsules and the like. Since it is more expensive and less convenient to administer such compositions, they are not preferred.

It is most preferred to administer compounds of this invention as additives to the animals' feed. Accordingly, feed compositions which contain a formula 1 compound are important embodiments of the invention.

Animal-feed compositions are usually prepared in stages. First, the compound is mixed with inert ingredients to prepare a feed premix, which is the form in which the compound is shipped from the original manufacturer to a local feed mill. Premixes may be either liquid or solid and may contain from about 1% to about 90% of the compound. The inert ingredients of a feed premix are not critical and may be any of the conventionally-used physiologically-acceptable carriers. Liquid carriers include, for example, glycols such as polyethylene glycols of various molecular weights and propylene glycol, inert oils including vegetable oils and refined mineral oil, and physiologically-acceptable alcohols such as ethanol. Solid premix carriers include, for example, verniculite, diatomaceous earth, physiologically-acceptable clays such as attapulgite and montmorillonite, and granulated or powdered feed components such as cracked corn, soybean meal, alfalfa meal, rice hulls, crushed corncobs, cracked wheat or oats and all sorts of waste materials of grain processing. Such ingredients of solid feed premixes are often granulated, pelleted or otherwise treated, as with dusting oils, to assure that the feed premix is not dusty and remains homogeneous.

The following are examples of feed premix compositions of the present invention.

| Ingredient | Percent |
|---|---|
| I | |
| ground oats | 94 |
| propylene glycol | 2 |
| lignin | 3 |
| formula 1 compound | 1 |
| II | |
| yellow corn | 24 |
| ground corn cobs | 25 |
| mineral oil | 1 |
| formula 1 compound | 50 |

A second stage in the manufacture of animal feeds is the feed supplement or concentrate. Such supplements are compositions in which the active compound is mixed with nutritive substances such as minerals, inorganic salts, trace elements and vitamins. Supplements are often mixed by diluting a feed premix with other constituents. A supplement may be used in the manufacture of complete mixed feed compositions containing a formula 1 compound or may be simply poured over unmedicated feed in the feed troughs or feed bunkers. The concentration of compounds in supplements varies widely, depending on the amount of the supplement to be fed to each animal. In general, concentrations in complete mixed feeds are from about 0.0005% to about 0.01%, preferably from about 0.002% to about 0.0075%. In general, concentrations in supplements to be poured over unmedicated feed in the feed troughs or feed bunks are from about 0.001% to about 0.5%, preferably from about 0.03% to about 0.3%. Examples of feed supplement compositions of this invention are the following:

| Ingredient | Percent |
|---|---|
| I | |
| ground corn cobs | 39.495 |
| soybean meal | 25.0 |
| ground corn | 20.0 |
| ground oats | 10.0 |
| molasses | 2.5 |
| salt | 0.4 |
| vitamin premix | 1.1 |
| animal fat | 1.5 |
| formula 1 compound | 0.005 |
| II | |
| soybean meal | 66.897 |
| milo | 25.5 |
| dicalcium phosphate | 2.1 |
| limestone | 1.2 |
| salt | 1.6 |
| molasses | 2.1 |
| trace minerals and vitamin premix | 0.6 |
| formula 1 compound | 0.003 |

Those skilled in the art of animal husbandry understand the conventional components of the animal feeds. Such feeds routinely are composed of basic grains and are supplemented with vitamins, minerals, inorganic salts and other important nutritive substances to assure that the animals are properly nourished. Feed should contain from about 10 to about 110 parts per million (ppm) (or 20 to 100 g/ton) of the compound; preferably, feeds should contain from about 25 to about 70 ppm (or 30 to 60 g/ton). The following are examples of feed compositions of this invention:

| Ingredient | Amount |
|---|---|
| I | |
| chopped alfalfa | 54.88% |
| sorghum grain | 36.20% |
| soybean meal | 4.10% |
| urea/grain mixture, 70% protein | 3.60% |
| dicalcium phosphate | 0.90% |
| trace mineralized salt | 0.23% |
| vitamin supplement | 0.09% |
| formula 1 compound | 25 ppm |
| II | |
| ground sorghum | 60.0% |
| alfalfa meal | 15.0% |
| cottonseed hulls | 15.0% |
| cottonseed meal | 8.5% |
| salt | 1.0% |
| ground limestone | 0.5% |
| formula 1 compound | 50 ppm |

In order to illustrate more fully the operation of this invention, the following examples are provided:

EXAMPLE 1

A. Shake-flask Fermentation of *S. spheroides* to Produce Factor S-1, Chloramphenicol, Cycloheximide, Septacidin, and Actiphenol A lyophilized pellet of Streptomyces spheroides NRRL 15600 is dispersed in 1–2 ml of sterilized water. This solution (<0.1 ml) is used to inoculate an agar slant having the following composition:

| Ingredient | Amount (%) |
|---|---|
| Potato dextrin | 1.0 |
| Enzymatic digest of casein | 0.2 |
| Yeast extract | 0.1 |
| Beef extract | 0.1 |
| $CoCl_2 \cdot 6H_2O$ | 0.001 |
| Deionized water | q.s. to 1 liter |

The inoculated slant is incubated at 30° C. for about 7 days. The mature slant culture is scraped with a sterile pipette or loop to loosen the spores. About one-fourth of the loosened spores are used to inoculate 50 ml of a vegetative medium having the following composition:

| Ingredient | Amount (%) |
|---|---|
| Glucose | 1.5 |
| Potato dextrin | 2.0 |
| Soybean grits | 1.5 |
| Yeast extract | 0.1 |
| Corn steep liquor | 1.0 |
| CaCO$_3$ | 0.2 |
| Tap water | q.s. to 1 liter |

Presterilization pH = 5.6; adjust to pH 6.5 with NaOH; poststerilization pH = 6.8.

The inoculated vegetative medium is incubated in a 250-ml wide-mouth Erlenmeyer flask at 30° C. for about 96 hours on a shaker orbiting in a 2-inch (5.08-cm) circle at 250 RPM.

This incubated vegetative medium (0.4 ml) is used to inoculate 50 ml of a production medium having the following composition:

| Ingredient | Amount (%) |
|---|---|
| Glucose | 2.5 |
| Starch (corn) | 1.0 |
| Soluble meat peptone$^a$ | 1.5 |
| Molasses (blackstrap) | 2.0 |
| MgSO$_4$.7H$_2$O | 0.05 |
| CaCO$_3$ | 0.2 |
| Tap water | q.s. to 100% |

$^a$O.M. Peptone, Amber Laboratories, Juneau, Wis 53039 Pre- and poststerilization pH = 6.2 (no adjustment)

The inoculated fermentation medium is incubated in a 250-ml wide-mouth Erlenmeyer flask at 30° C. for about 5 to 6 days on a shaker orbiting in a 2-inch circle at 250 RPM.

B. Tank Fermentation of *S. spheroides* to Produce Factor S-1, Chloramphenicol, Cycloheximide, Septacidin and Actiphenol In ordr to provide a larger volume of inoculum, 10 ml of incubated vegetative medium, prepared in a manner similar to that described in section A, is used to inoculate 400 ml of a second-stage vegetative growth medium having the same composition as that of the vegetative medium. This second-stage vegetative medium is incubated in a 2-liter flask for about 48 hours at 30° C. on a shaker orbiting in a 2-inch circle at 250 RPM.

Incubated second-stage medium (800 ml) thus prepared is used to inoculate 100 liters of sterile production medium having the same composition as that in Sect. A.

The inoculated production medium is allowed to ferment in a 165-liter tank for 5 to 7 days at a temperature of 30° C. The fermentation medium is aerated with sterile air to keep the dissolved oxygen level between about 30% and 60% and is stirred with conventional agitators at about 200 RPM.

EXAMPLE 2

Isolation of Factor S-1, Chloramphenicol and Cycloheximide

Whole broth (100 L), prepared in a manner similar to that of Example 1, Section B, was filtered using a filter aid (Hyflo Supercel, Johns-Manville Corp.). The filtered broth (86 L) is adjusted to pH 2 with 5N hydrochloric acid and then is extracted twice with ethyl acetate (½ volumes). The ethyl acetate extracts are concentrated under vacuum to give an oily residue (49 g). This residue is dissolved in methanol and placed on a 10-L Diaion HP-20 column (Mitsubishi Industries). The column is washed with water (500 ml) and eluted with acetonitrile:water (30 L of 3:7 and 50 L of 3:2) and acetonitrile (20 L). Elution is carried out at a rate of 100 ml/min., collecting 4-liter fractions. Fractions are tested for antibiotic activity against *Micrococcus luteus, Escherichia coli,* and *Neurospora crassa.*

Cycloheximide, which is active against *N. crassa,* is eluted in early 3:7 fractions. Chloramphenicol, which is active against *E. coli,* is eluted in later 3:7 fractions. Factor S-1, which is active against *M. luteus,* is eluted in 3:2 fractions. Fractions containing factor S-1 are combined and concentrated under vacuum to give an oily residue (7.65 g).

This residue is chromatographed on a 1.9-L silica-gel column (grade 62, Matheson, Coleman and Bell). The column is eluted with chloroform:methanol:ammonium hydroxide (90:9.5:0.5; 2.5 L) at a rate of 20 ml/min. Fractions are combined on the basis of color (yellow and red) and activity against *M. luteus.* Fractions from the red-colored band are concentrated under vacuum to give an oil. This oil is dissolved in tetrahydrofuran (100 ml), and product is precipitated by adding the solution to hexane (15 volumes). The precipitate is separated to give 1.2 g of factor S-1.

Factor S-1 is further purified in 200-mg portions by dissolving it in methanol and chromatographing the solution on a 1"×30-cm column packed with Zorbax ODS (12μ) (E. I. duPont). The column is eluted at 10 ml/min with 45% acetonitrile in 0.01% trifluoroacetic acid (400 ml) and then with a 400-ml gradient of from 45%-100% acetonitrile in 0.01% trifluoroacetic acid. Fractions are checked by UV absorption at 264 nm and by disc bioassay against *M. luteus.* Fractions containing only factor S-1 are combined, concentrated and lyophilized to dryness. Fractions containing factor S-1 with other material are concentrated and rechromatographed on a preparative HPLC column. Approximately 800 mg of purified factor S-1 is obtained from 100 L of fermentation broth.

We claim:

1. Antibiotic A39079 factor S-1 which in its reduced form has structure 1:

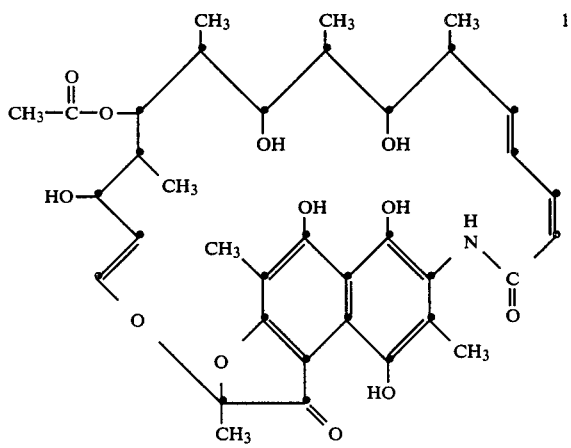

and which in its oxidized form has structure 2

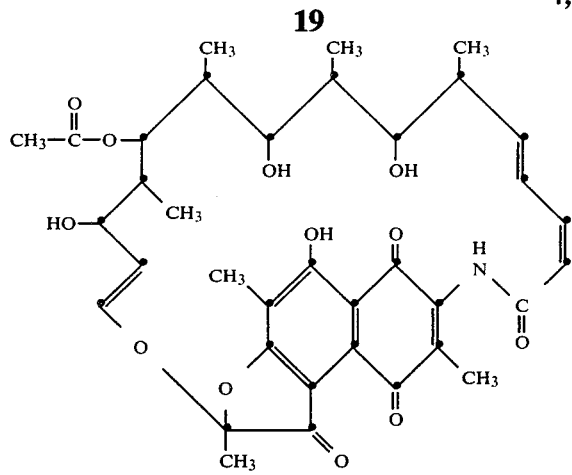
2. The compound of claim 1 which is A39079 factor S-1 in the oxidized form.
3. The compound of claim 1 which is A39079 factor S-1 in the reduced form.
4. The $C_2$–$C_{18}$-mono- or di-carboxylic acid ester derivatives of A39079 factor S-1.
5. A compound of claim 4 wherein the ester is a pharmaceutically acceptable ester.
* * * * *